United States Patent
De Sousa

(10) Patent No.: US 9,173,405 B2
(45) Date of Patent: Nov. 3, 2015

(54) HERBICIDE FORMULATION

(75) Inventor: Ubiratan Ferreira De Sousa, São Caetano do Sul-SP (BR)

(73) Assignee: OXITENO S.A. INDUSTRIA E COMERCIO, Sao Paulo (BR)

( * ) Notice: Subject to any disclaimer, the term of this patent is extended or adjusted under 35 U.S.C. 154(b) by 676 days.

(21) Appl. No.: 12/988,253

(22) PCT Filed: Apr. 18, 2008

(86) PCT No.: PCT/BR2008/000110
§ 371 (c)(1),
(2), (4) Date: Dec. 2, 2010

(87) PCT Pub. No.: WO2009/127020
PCT Pub. Date: Oct. 22, 2009

(65) Prior Publication Data
US 2011/0263426 A1    Oct. 27, 2011

(51) Int. Cl.
*A01N 57/20* (2006.01)
*A01N 25/30* (2006.01)

(52) U.S. Cl.
CPC ..................... *A01N 57/20* (2013.01)

(58) Field of Classification Search
CPC ....................................... A01N 57/20
USPC ........................................ 504/128
See application file for complete search history.

(56) References Cited

FOREIGN PATENT DOCUMENTS

| EP | 0 274 369 A1 | 7/1988 |
| EP | 360181 A2 * | 3/1990 |
| WO | WO 01/17346 A1 | 3/2001 |
| WO | WO 2004/019681 A2 | 3/2004 |

OTHER PUBLICATIONS

Bieringer, H., Salts of Herbicidal Acids with Long-Chain Nitrogen Bases, EP360181-A2, Mar. 1990, Translation, 9 pages.*

* cited by examiner

*Primary Examiner* — Sue Liu
*Assistant Examiner* — Andriae M Holt
(74) *Attorney, Agent, or Firm* — Birch, Stewart, Kolasch & Birch, LLP

(57) ABSTRACT

The invention relates to a herbicide formulation comprising a water soluble salt of n-phosphomethylglycine and at least one adjuvant, the said adjuvant consisting in an alkoxylated imidazoline with the following structure I

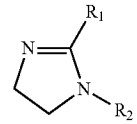

wherein $R_1$ is a saturated or unsaturated C4 to C24 fatty acid. The use of the alkoxylated imidazoline provides as a result a herbicide formulation that is not irritant to the skin or the eyes. Furthermore, the adjustment of the degree of ethoxylation or propoxylation of the imidazoline permits the compatibility thereof with the various glyphosate salts, allowing the obtainment of concentrated solutions that maintain stability at temperatures higher than 60° C., without requiring other adjuvants.

8 Claims, No Drawings

HERBICIDE FORMULATION

FIELD OF THE INVENTION

The present invention refers to herbicides, particularly to herbicides with foliar activity, and more particularly to herbicides that employ glyphosate as active ingredient.

SUMMARY OF THE PRIOR ART

Due to significant scientific/technological progress, society as a whole is challenged on a daily basis with a process of environmental degradation, which on a short or a long term destabilizes the ecological system, thereby disrupting the (trophic) food chain. Such fact triggers an unbalanced proliferation of certain species, particularly noxious weeds, which originated and developed along with agricultural processes by means of an evolution process, accumulating characteristics that allow the coexistence thereof with the cultures, thereby occupying ecological niches not exploited by the cultivated plant.

In the course of the evolution process the said noxious weeds acquired biological characteristics of great aggressiveness, mainly related to a high capacity to compete for water, light and nutrients, in addition to possible allelopathic effects of some species in search of new food resources, and came to represent a factor of competition to the human species.

With the objective of controlling said proliferation including high technology and low production cost, there has been developed a range of products/techniques, and among the most versatile of these, there is pointed out the glyphosate (n-phosphomethylglycine), which formula is reproduced in FIG. 1. Discovered by the Monsanto company in 1970, it received the commercial name 'Roundup' in 1974, and was thereafter used in large scale upon introduction of the direct planting (no-tillage) practice.

This product is a herbicide belonging to the chemical group of substituted glycines, classed as non-selective and having systemic activity, with a large spectrum of activity, and which is basically absorbed by the chlorophyll region of plants (green tissue and leaves) and transported to the meristematic tissues by the phloem. The glyphosate acts in various manners, inhibiting the synthesis of chlorophyll, stimulating the production of ethylene, reducing the synthesis of proteins, in addition to being a potent inhibitor of the activity of 5-enolpyruvylshikimate-3-phosphate-synthase (EPSPS), which is the catalyst of one of the synthesis reactions of the amino acids phenylalanine, tyrosine and tryptophan.

From the perspective of impact on the ecological system, the glyphosate evidences the following characteristics:
- it is virtually nontoxic to mammals, birds, fish, insects and the majority of bacteria;
- the glyphosate does not entail bio-accumulation in the tissues of animals or plants of agronomical importance. It is classified with the least toxicity level according to the EPA, the Environment Protection Agency of the United States of America;
- it does not evidence signs of mutagenicity, carcinogenicity or teratogenicity.
- it does not evidence residual activity on the soil, even when applied in large dosage amounts.

One important characteristic of the glyphosate is its ability to be adsorbed by the particles of the soil, remaining inactive until its complete degradation. The adsorption of the glyphosate occurs in practically all types of soil: when applied in red-yellow clay soil of medium texture, the half-life of the glyphosate was only 8 to 9 days; in the case of clayish latosoil, this period is of the order of 12 days. The degradation of the glyphosate adsorbed into the soil is very rapid and is realized by a great variety of microorganisms that use this product as a source of energy and phosphorus supply, by means of two catabolic routes. In one of these, the main metabolite is aminomethyl phosphonic acid (AMPA), and in the alternative route, the intermediary metabolite is sarcosine.

Notwithstanding the obvious advantages of its use in the control of noxious weeds, the glyphosate molecule evidences polar characteristics that restrict its capacity to cross the serous layer that coats the leaves. Furthermore, the cell wall, although permeable to water soluble compounds, is also negatively charged. It is therefore necessary to use an adjuvant to enable the crossing of these barriers and to allow the glyphosate to penetrate into the phloem to be carried to the other parts of the plant.

In order to solve the cited problem, the original patent U.S. Pat. No. 3,799,758 included in the herbicide formulation a surface-active adjuvant, comprising, among others; alkyl benzene sulfonates or alkyl naphthalene sulfonates, sulfated fatty alcohols, amines or acid amines, long chain acid esters of sodium isothionate, esters of sodium sulfosuccinate, sulfonated vegetable oils, ditertiary acetylenic glycols and ethoxylated alkyl amine, the latter being preferred in the majority of the classic formulations due to its low cost and reasonable efficiency.

However, the use of the known surfactant agents in the glyphosate-based formulations has some problems. The first of these problems is due to the fact that the molecule depicted in FIG. 1 is poorly soluble in water. Therefore, the compound normally used in the herbicide formulations is a salt, obtained by neutralizing the n-phosphomethylglycine with a base, using most frequently ammonia, potassium, monoethanolamine (MEA) and monoisopropanolamine (MIPA). However, when adding the surfactant agent to a concentrated saline solution, there may occur the segregation of these components, such phenomenon being known in the art as salting-out. In actual practice, it is initially observed that the solution becomes turbid ("cloud point") followed by the separation of the surfactant agent dissolved in the water which floats on the surface while the saline solution precipitates towards the bottom. The addition of a glycol or an alcohol allows to avoid such segregation in concentrated solutions that are commercialized for later dilution on the field. Thus, for example, a typical commercial solution contains 480 g/l of glyphosate, 100 g/l of ethoxylated alkyl amine and 50 g/l of ethanol or glycol. Since in these solutions there is used approximately 30% ethanol or glycol, this means that the availability of the surface-active agent is reduced in the same proportion, which causes a lesser efficiency of the final product.

One other disadvantage of the ethoxylated alkyl amine resides in the fact of the same being irritating to the skin and the eyeball, requiring special care during the handling and application of the herbicide.

One further disadvantage consists in the fact that different glyphosate salts evidence various degrees of compatibility with certain surfactants, to the point of even rendering impossible the use of certain formulations.

OBJECTS OF THE INVENTION

In light of the above, the object of the present invention consists in the provision of a glyphosate-based herbicide formulation that does not require the addition of glycols or alcohols.

One other object consists in the provision of a formulation that is not irritating, thereby avoiding the need of special precautions in the handling and application thereof.

One other object consists in enabling the obtainment of formulations using various glyphosate salts.

One other object consists in increasing the availability of surfactant agents in the formulation.

Lastly, one further object consists in providing an improvement of the performance of the herbicide formulation.

SUMMARY OF THE INVENTION

The above listed and other objects are achieved by the invention by means of the provision of a herbicide formulation that comprises the incorporation of alkoxylated imidazoline as an adjuvant for saline solutions of glyphosate, wherein the alkoxylated imidazoline has the following structure I:

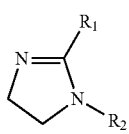

wherein $R_1$ is a saturated or unsaturated C4 to C24 fatty acid, and $R_2$ is one of the compounds listed in the following:
  ethylene polyoxide (—$CH_2CH_2O$—)$_n$H, wherein n>1
  propylene polyoxide (—$CHCH_3CH_2O$—)$_n$H, wherein n>1
  ethylene and propylene polyoxide (—$CH_2CH_2O$—)$_n$(—$CHCH_3CH_2O$—)$_m$H, wherein n+m>1
  alkoxylated ethylene amine

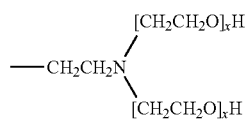

wherein x+y is a number between 0 and 100.

According to another characteristic of the invention, the said fatty acid comprises alkyl or hydroxyl groups bound to the carbon chain.

According to another characteristic of the invention, the said fatty acid is reacted with aminoethyethanolamine or with diethylenetriamine in two steps, there being produced amidoamine in the first step, and in the second step, by means of withdrawal of 1 mole of water, there being produced imidazoline.

According to another characteristic of the invention, there are used vegetable oils as a source of fatty acids.

According to another characteristic of the invention, there is provided compatibility between the alkoxylated imidazoline and the various glyphosate salts by means of adjustment of the degree of ethoxylation or propoxylation.

According to another characteristic of the invention, the formulation may comprise, in addition to the glyphosate salt and the alkoxylated imidazoline, other surface active agents, glycols, alcohols, glycolic ethers or glycerol.

According to another characteristic of the invention, the formulation may be provided in liquid or solid form.

DETAILED DESCRIPTION OF THE INVENTION

The present invention is based on the fact that the substitution of the ethoxylated alkyl amine with an alkoxylated imidazoline produces as a result a herbicide formulation that does not cause irritation to the skin or to the eyes. Unexpectedly, it was found that the adjustment of the degree of ethoxylation or propoxylation of the imidazoline enables the achievement of compatibility thereof with the various salts of glyphosate, allowing the obtainment of concentrated solutions that maintain stability at temperatures higher than 60° C. without requiring other co-adjuvants. Thus, a variation of the number of moles of ethylene oxide within a range comprised between 2 and 25 per mole of imidazoline allows the achievement of compatibility thereof with salts based on monoisopropanolamine (MIPA), monoethanolamine (MEA), ammonia and potassium. The alkoxylated imidazoline further has anticorrosive properties, such fact being of great importance to preserve the equipment used for application thereof in the field.

Amidoamines and imidazolines can be prepared from fatty acids or directly from oils and fats by means of reaction with various polyamines. The reaction below exemplifies the obtainment of a substituted imidazoline from the reaction of a fatty acid with aminoethylethanolamine and its subsequent ethoxylation, producing as a result a polyethoxylated imidazoline:

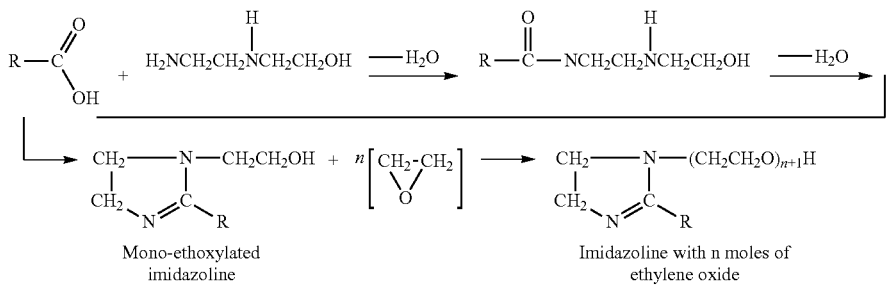

Mono-ethoxylated imidazoline

Imidazoline with n moles of ethylene oxide

In the above reactions, R is a C4 to C24 fatty acid, saturated or unsaturated, and may contain alkyl or hydroxyl groups linked to the carbon chain, such as butyric (C4), valeric (C5), caproic (C6), heptanoic (C7), capric (C8), nonanoic (C9), caprylic (C10), undecanoic (C11), laurylic (C12), tridecanoic (C13), myristic (C14), pentadecanoic (C15), palmitic (C16), cis-9-hexadecanoic (C16:1), heptadecanoic (C17), cis-9-heptadecenoic (C17:1), stearic (C18), oleic (C18:1), linoleic (C18:2), linolenic (C18:3), α-eleostearic (C18:3), ricinoleic or 12-hydroxy-cis-9-octadecenoic (C18:1), di-hydroxy stearic (C18), nonadecanoic (C19), arachidic (C20), arachidonic (C20:4), Eicosapentaenoic (C20:5), heneicosanoic (C21), behenic (C22), erucic (C22:1), Docosahexaenoic (C22:6), tricosanoic (C23), lignoceric (C24), among others.

The monoethoxylated imidazoline may be used in applications wherein a partial solubility in water is admissible, such as fabric softeners and cosmetics. The increased solubility required for the applications to which the present invention refers can be obtained by increasing the degree of ethoxylation, within an ample range of values: in the present invention, these values vary between 2 and 50. An unexpected effect observed when using ethoxylated imidazoline as adjuvant in the formulation is that—contrary to what occurs with alkyl amine—there does not occur the formation of gel upon dissolution in water, and therefore one may dispense the use of glycol or equivalent substance in the formulation.

As mentioned herein, there are advantageously used in the present invention those derived from C6 to C24 chain fatty acids, either or not unsaturated, which may contain hydroxyl groups linked to the chain, such as Ricinoleic Acid. These acids are reacted with Aminoethyethanolamine (AEEA) or Diethylenetriamine (DETA) in two steps, whereby in the first step there is produced the Amidoamine and in the second step there is produced the imidazoline by means of the withdrawal of one mole of water. The imidazoline generated by this process may be alkoxylated with ethylene oxide and/or with propylene oxide. Alternatively there may be used vegetable oils as the source of fatty acids. In this case, there is free glycerin in the produced Imidazoline and ethoxylated glycerin in the final product.

Particularly, the said ethoxylated imidazolines (IMIEt) can replace the Ethoxylated Fatty Amines and other surfactant agents as adjuvants in glyphosate herbicide formulations. The advantages of the use of IMIEt are: a simpler process for obtainment of the imidazolines relatively to Fatty Amines;

The imidazolines are liquid and are easier to handle than fatty amines;

They have anticorrosive properties and low irritability to the skin and the eyes, such characteristics being transferred to the glyphosate formulation;

They are soluble in water and do not require the addition of glycols or glycolic esters to avoid the formation of gels;

They allow the formulation of various glyphosate salts, such as potassium, MEA and MIPA;

They increase the solubility of nonionic surfactants in glyphosate solutions, such as EO fatty alcohols, EO fatty acids, polysorbates, among others.

The examples set forth below illustrate the advantages of the invention without however limiting the same. In all examples there was prepared a solution of glyphosate salt and there was added thereto an IMIEt or a combination thereof with other surfactant agents and/or glycols and glycolic ethers. The said salts were obtained by neutralizing the acid n-phosphomethylglycine by means of MIPA (monoisopropanolamine), MEA (monoethanolamine) and K (potassium). There were used imidazolines with degrees of ethoxylation varying between 3 (moles of ethylene oxide per mole of imidazoline) and 15. As may be noted in these examples, there are preferentially used imidazolines derived from saturated and unsaturated acids, comprising lauric, oleic and ricinoleic acids, there being pointed out, however, that these examples are not limitative to the scope of the invention.

The stability of the formulations was evaluated as a function of the temperature at which occurred the onset of turbidity, such temperature being designated as the Cloud Point of the formulation (CP). A formulation is deemed stable if it appears limpid immediately after the addition of the adjuvant and if the solution remains limpid above 60° C. When the cloud point occurs below 25° C., such fact means that there occurred a separation of phases at the moment of formulation of the product, and the formulation is thereby deemed unstable.

Examples

| Ex. | Salt | Glyphosate (g of e.a./l) | Adjuvant Composition | % of adjuvant | CP |
|---|---|---|---|---|---|
| 1 | MIPA | 360 | Lauric Imidazoline 6 EO | 12 | >60° C. |
| 2 | MIPA | 360 | Oleic Imidazoline 5 EO | 12 | >60° C. |
| 3 | MIPA | 360 | Oleic Imidazoline 10 EO | 12 | >60° C. |
| 4 | MIPA | 360 | Oleic Imidazoline 15 EO | 12 | >60° C |
| 5 | MIPA | 360 | Oleic Imidazoline 15 EO | 18 | >60° C. |
| 6 | MIPA | 360 | Ricinoleic Imidazoline 5 EO | 12 | >60° C. |
| 7 | MIPA | 360 | Ricinoleic Imidazoline 15 EO | 12 | >60° C. |
| 8 | MIPA | 360 | Ricinoleic Imidazoline 15 EO | 18 | >60° C. |
| 9 | MIPA | 360 | 50% Oleic Imidazoline 15 EO 35% Fatty Amine 15 EO 10% Monoethyleneglycol 5% Water | 12 | >60° C. |
| 10 | MIPA | 360 | 80% Oleic Imidazoline 15 EO 20% Ketostearylic Alcohol 20 EO | 12 | >60° C. |
| 11 | MIPA | 360 | 20% Oleic Imidazoline 15 EO 80% Ketostearylic Alcohol 20 EO | 12 | <25° C. |
| 12 | MIPA | 360 | 75% Oleic Imidazoline 15 EO 25% Polysorbate 80 | 12 | >60° C. |
| 13 | MIPA | 360 | 50% Oleic Imidazoline 15 EO 50% Polysorbate 80 | 12 | <25° C. |
| 14 | K | 540 | 60% Oleic Imidazoline 5EO 5% Oleic Imidazoline 15EO 35% MEG GI | 12 | <25° C. |
| 15 | K | 540 | Oleic Imidazoline 5 EO | 12 | <25° C. |
| 16 | K | 540 | Oleic Imidazoline 5 EO | 3 | >60° C. |
| 17 | K | 540 | Oleic Imidazoline | 12 | <25° C |
| 18 | K | 540 | 60% Oleic Imidazoline 5 EO MEG (40%) | 12 | <25° C. |
| 19 | K | 540 | 60% Oleic Imidazoline 2 EO 40% MEG | 12 | >60° C. |

-continued

| Ex. | Salt | Glyphosate (g of e.a./l) | Adjuvant Composition | % of adjuvant | CP |
|---|---|---|---|---|---|
| 20 | K | 540 | 60% Oleic Imidazoline 2 EO<br>40% Butylglycol | 12 | >60° C. |
| 21 | K | 540 | 50% Oleic Imidazoline 2 EO<br>33% Amine 5 EO<br>17% Monoethyleneglycol | 12 | >60° C. |
| 22 | MEA | 360 | 50% Oleic Imidazoline 2 EO<br>50% Monoethyleneglycol | 12 | >60° C. |
| 23 | MEA | 360 | 50% Oleic Imidazoline 2 EO<br>50% Butylglycol | 12 | >60° C. |
| 25 | MEA | 360 | 50% Oleic Imidazoline 2 EO<br>33% Amine 5 EO<br>17% Monoethyleneglycol | 12 | >60° C. |

The invention claimed is:

1. A herbicide formulation, characterized by comprising a water soluble salt of monoisopropylamine (MIPA) glyphosate and at least one alkoxylated imidazoline, wherein said alkoxylated imidazoline is in an amount of 6 to 18% in mass percentage and consists of the following structure I

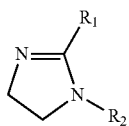

wherein $R_1$ is the aliphatic carbon chain of lauric acid, oleic acid, or ricinoleic acid; and $R_2$ represents ethylene polyoxide having the structure $(-CH_2CH_2O-)_nH$, wherein n is within a range of between 5 and 15.

2. A herbicide formulation, as claimed in claim 1, characterized in that the formulation further comprises other surface active agents, glycols, alcohols, glycolic ethers or glycerol.

3. The herbicide formulation according to claim 1, characterized in that the formulation may be provided in liquid or solid form.

4. A herbicide formulation, characterized by comprising a water soluble salt of potassium (K) or monoethanolamine (MEA) glyphosate and at least one alkoxylated imidazoline, wherein said alkoxylated imidazoline is in an amount of 3 to 12% in mass percentage and consists of the following structure I

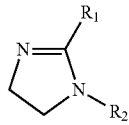

wherein $R_1$ is the aliphatic carbon chain of oleic acid; and
$R_2$ represents ethylene polyoxide having the structure $(-CH_2CH_2O-)_nH$, wherein n is 2.

5. The herbicide formulation, as claimed in claim 1, wherein the alkoxylated imidazoline is in an amount of 12 to 18% in mass percentage.

6. The herbicide formulation, as claimed in claim 4, characterized in that the formulation may be provided in liquid or solid form.

7. A herbicide formulation, as claimed in claim 4, characterized in that the formulation further comprises other surface active agents, glycols, alcohols, glycolic ethers or glycerol.

8. The herbicide formulation, as claimed in claim 4, wherein the alkoxylated imidazoline is in an amount of 6 to 7.2% in mass percentage.

* * * * *